(12) United States Patent
Hata et al.

(10) Patent No.: US 10,198,813 B2
(45) Date of Patent: Feb. 5, 2019

(54) POSTURE ESTIMATION DEVICE, POSTURE ESTIMATION SYSTEM, POSTURE ESTIMATION METHOD, POSTURE ESTIMATION PROGRAM, AND COMPUTER-READABLE RECORDING MEDIUM ON WHICH POSTURE ESTIMATION PROGRAM IS RECORDED

(71) Applicants: OMRON Corporation, Kyoto-shi, Kyoto (JP); UNIVERSITY OF HYOGO, Kobe-shi, Hyogo (JP)

(72) Inventors: Yutaka Hata, Himeji (JP); Hiroshi Nakajima, Kyoto (JP); Yusuke Taniguchi, Kakogawa (JP); Fumiji Aita, Nara (JP); Junichi Tanaka, Kyotanabe (JP); Naoki Tsuchiya, Otsu (JP)

(73) Assignees: OMRON Corporation, Kyoto-shi (JP); UNIVERSITY OF HYOGO, Kobe-shi (JP)

( * ) Notice: Subject to any disclaimer, the term of this patent is extended or adjusted under 35 U.S.C. 154(b) by 0 days.

(21) Appl. No.: 15/307,594

(22) PCT Filed: Apr. 22, 2015

(86) PCT No.: PCT/JP2015/062215
§ 371 (c)(1),
(2) Date: Oct. 28, 2016

(87) PCT Pub. No.: WO2015/174228
PCT Pub. Date: Nov. 19, 2015

(65) Prior Publication Data
US 2017/0053401 A1    Feb. 23, 2017

(30) Foreign Application Priority Data
May 13, 2014  (JP) ................. 2014-099347

(51) Int. Cl.
*G06T 7/00* (2017.01)
*A61B 5/107* (2006.01)
(Continued)

(52) U.S. Cl.
CPC ............ *G06T 7/0012* (2013.01); *A61B 5/107* (2013.01); *A61B 5/11* (2013.01); *A61B 5/1115* (2013.01);
(Continued)

(58) Field of Classification Search
CPC .......... G06K 9/00335; G06K 9/00362; G06K 9/4604; G06K 9/52; G06K 2009/4666;
(Continued)

(56) References Cited

U.S. PATENT DOCUMENTS 9,704,372 B2 * 7/2017 Van Oorschot ........... A61F 5/56
9,799,376 B2 * 10/2017 Wang ..................... G11B 27/34
(Continued)

FOREIGN PATENT DOCUMENTS

| | | |
|---|---|---|
| CN | 1939215 A | 4/2007 |
| JP | 2006-175082 A | 7/2006 |

(Continued)

OTHER PUBLICATIONS

The extended European search report (EESR) dated Jan. 8, 2018 in a counterpart European patent application.
(Continued)

*Primary Examiner* — Mekonen Bekele
(74) *Attorney, Agent, or Firm* — Metrolexis Law Group, PLLC

(57) ABSTRACT

An image acquisition part acquires image data from an image sensor provided in a room. A storage stores information indicating a transition model of a human body posture and test information indicating a test area of the image data in each posture of the transition model. A posture estimator
(Continued)

calculates a statistic in the test area of the image data by referring to the information indicating the transition model and the test information, and estimates a current human body posture from a human body posture before one point of time based on the statistic.

16 Claims, 13 Drawing Sheets

(51) Int. Cl.
*A61B 5/11* (2006.01)
*G06T 7/60* (2017.01)
*G06K 9/00* (2006.01)
*G06K 9/46* (2006.01)
*G06K 9/52* (2006.01)

(52) U.S. Cl.
CPC .......... *A61B 5/1116* (2013.01); *A61B 5/1117* (2013.01); *G06K 9/00335* (2013.01); *G06K 9/00362* (2013.01); *G06K 9/4604* (2013.01); *G06K 9/52* (2013.01); *G06T 7/60* (2013.01); *G06K 2009/4666* (2013.01); *G06T 2207/10048* (2013.01); *G06T 2207/30004* (2013.01)

(58) Field of Classification Search
CPC ................. G06T 7/0012; G06T 7/60; G06T 2207/10048; G06T 2207/30004; A61B 5/107; A61B 5/11; A61B 5/1115; A61B 5/1116; A61B 5/1117
See application file for complete search history.

(56) References Cited

U.S. PATENT DOCUMENTS

| | | | |
|---|---|---|---|
| 2007/0268295 A1 | 11/2007 | Okada | |
| 2009/0044334 A1 | 2/2009 | Parsell et al. | |
| 2010/0235151 A1* | 9/2010 | Yoneda | G06F 19/3437 703/2 |
| 2013/0100284 A1 | 4/2013 | Fujii et al. | |
| 2013/0215248 A1* | 8/2013 | Ishii | A61B 5/1113 348/77 |
| 2014/0211003 A1* | 7/2014 | Lee | H04N 7/181 348/143 |
| 2015/0036914 A1* | 2/2015 | Sekiguchi | H01J 37/3174 382/149 |
| 2015/0110406 A1* | 4/2015 | Ohashi | H01J 37/222 382/199 |
| 2016/0078297 A1* | 3/2016 | Wang | G11B 27/105 386/241 |
| 2017/0309016 A1* | 10/2017 | Klaiman | A61B 6/4441 |

FOREIGN PATENT DOCUMENTS

| | | |
|---|---|---|
| JP | 4579865 B2 | 11/2010 |
| JP | 2015-079339 A | 4/2015 |
| WO | 2011016782 A1 | 2/2011 |
| WO | 2012/001473 A1 | 1/2012 |
| WO | 2014/012070 A1 | 1/2014 |

OTHER PUBLICATIONS

The Chinese Office Action (CNOA) issued on Oct. 15, 2018 in a counterpart Chinese Patent application.

* cited by examiner

| Area | X-direction | Y-direction |
|---|---|---|
| RV1 | 0≤X≤15 | 0≤Y≤15 |
| RV2 | 7≤X≤9 | 3≤Y≤10 |
| RV3 | 3≤X≤6 | 3≤Y≤10 |
| RV4 | 0≤X≤2<br>7≤X≤15<br>3≤X≤6<br>3≤X≤6 | 0≤Y≤15<br>0≤Y≤15<br>0≤Y≤2<br>11≤Y≤15 |

| Area | X-direction | Z-direction |
|---|---|---|
| RH1 | 0≤X≤15 | 0≤Z≤15 |
| RH2 | 8≤X≤10 | 0≤Z≤15 |
| RH3 | 11≤X≤15 | 5≤Z≤9 |
| RH4 | 11≤X≤15 | 7≤Z≤9 |
| RH5 | 0≤X≤10 | 10≤Z≤15 |
| RH6 | 0≤X≤10 | 10≤Z≤12 |

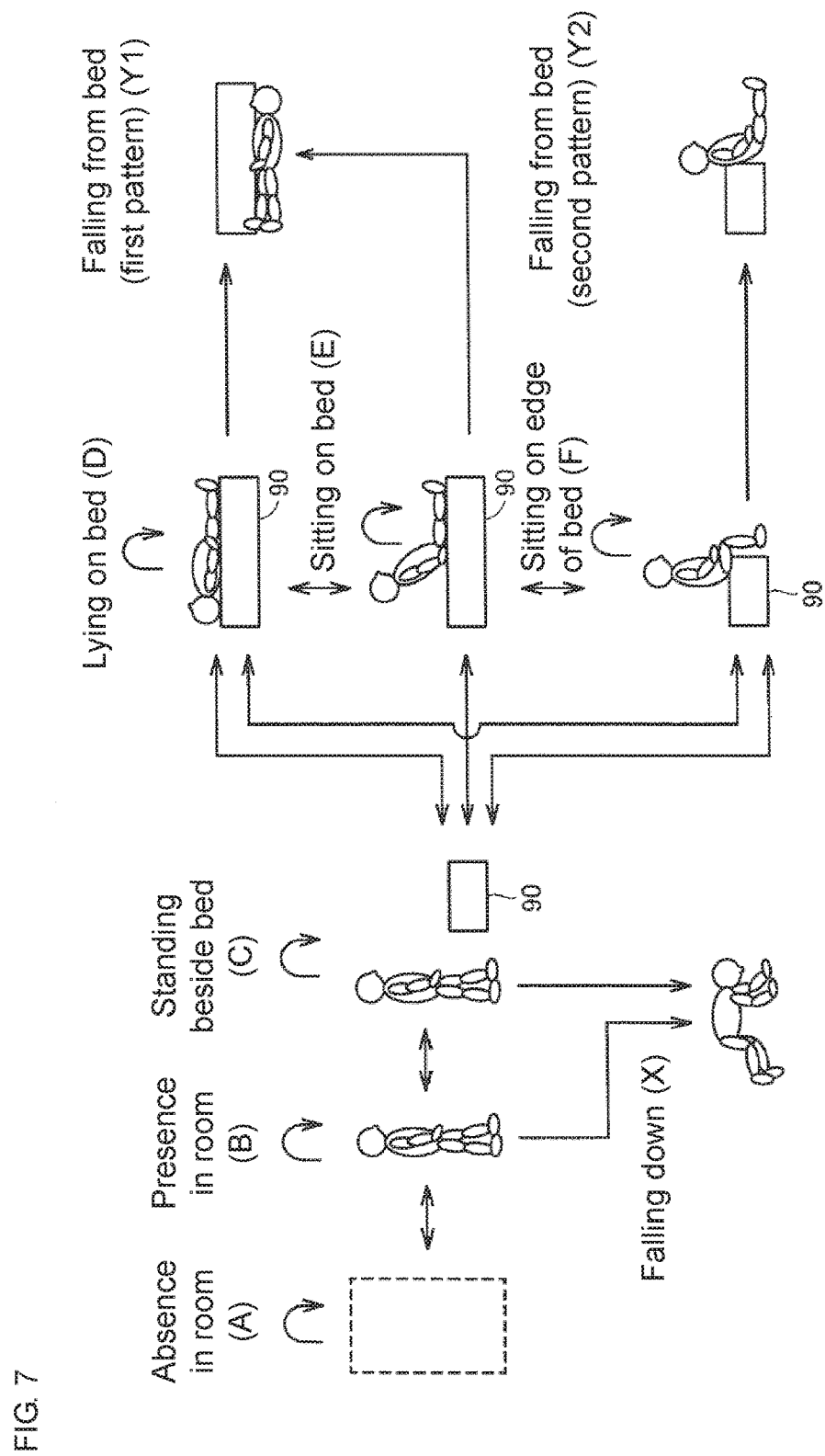

FIG. 8

| Posture estimated before one point of time | Current posture candidate |
|---|---|
| Absence in room (A) | Presence in room (B)<br>Absent in room (A) [Unchanged] |
| Presence in room (B) | Standing beside bed (C)<br>Falling down (X)<br>Absence in room (A)<br>Presence in room (B) [Unchanged] |
| Standing beside bed (C) | Lying on bed (D)<br>Sitting on bed (E)<br>Sitting on edge of bed (F)<br>Falling down (X)<br>Presence in room (B)<br>Standing beside bed (C) [Unchanged] |
| Lying on bed (D) | Sitting on bed (E)<br>Sitting on edge of bed (F)<br>Standing beside bed (C)<br>Falling from bed (first pattern) (Y1)<br>Lying on bed (D) [Unchanged] |
| Sitting on bed (E) | Lying on bed (D)<br>Sitting on edge of bed (F)<br>Standing beside bed (C)<br>Falling from bed (first pattern) (Y1)<br>Sitting on bed (E) [Unchanged] |
| Sitting on edge of bed (F) | Lying on bed (D)<br>Sitting on bed (E)<br>Standing beside bed (C)<br>Falling from bed (second pattern) (Y2)<br>Sitting on edge of bed (F) [Unchanged] |

FIG. 9

| Posture | Test area of first image data | Test area of second image data | Reference value |
|---|---|---|---|
| Absence in room (A) | RV1 | RH1 | THA |
| Presence in room (B) | RV1 | RH1 | THB |
| Standing beside bed (C) | RV2 | RH2 | THC |
| Lying on bed (D) | RV3 | RH4 | THD |
| Sitting on bed (E) | RV3 | RH3 | THE |
| Sitting on edge of bed (F) | RV3 | RH2 | THF |
| Falling down (X) | RV4 | RH5 | THX |
| Falling from bed (first pattern) Y1 | RV2 | RH6 | THY1 |
| Falling from bed (second pattern) Y2 | RV2 | RH6 | THY2 |

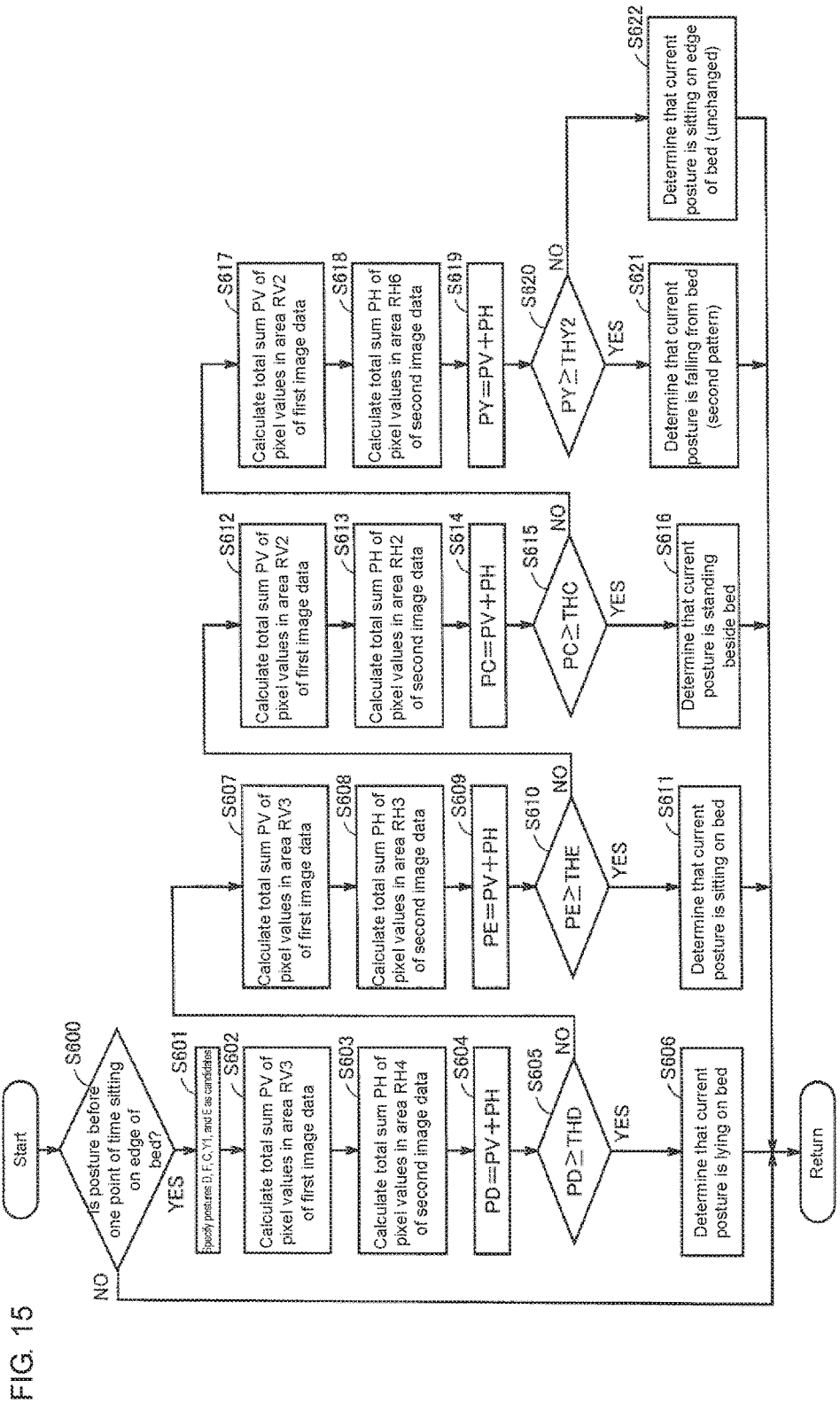

POSTURE ESTIMATION DEVICE, POSTURE
ESTIMATION SYSTEM, POSTURE
ESTIMATION METHOD, POSTURE
ESTIMATION PROGRAM, AND
COMPUTER-READABLE RECORDING
MEDIUM ON WHICH POSTURE
ESTIMATION PROGRAM IS RECORDED

TECHNICAL FIELD

The present invention relates to a posture estimation device, a posture estimation system, a posture estimation method, and a posture estimation program for estimating a posture of a human body in a room, and a computer-readable recording medium on which the posture estimation program is recorded.

BACKGROUND ART

Conventionally, there is known a device that monitors a behavior of a person, such as an elderly person, who needs nursing care.

For example, Patent Document 1 (Japanese Unexamined Patent Publication No. 2006-175082) discloses a device in which, in order to determine whether a care receiver lying on a bed performs a rising behavior, a watching area is set above the bed, and an image of the watching area is captured with a camera from a lateral direction of the bed. The device estimates that the care receiver performs the rising behavior when a ratio of an image area of the care receiver to the watching area of the image captured with the camera is a predetermined value or more.

PRIOR ART DOCUMENT

Patent Document

Patent Document 1: Japanese Unexamined Patent Publication No. 2006-175082

SUMMARY OF THE INVENTION

Problems to be Solved by the Invention

However, in the device of Patent Document 1, it is necessary to perform image processing to specify the image area of the care receiver because the device estimates that the care receiver performs the rising behavior when the ratio of the image area of the care receiver to the watching area is a predetermined value or more. Resultantly, a data processing amount increases, and a change in posture cannot be estimated in real time.

An object of the present invention is to provide a posture estimation device, a posture estimation system, a posture estimation method, and a posture estimation program for estimating a posture of a human body in a room with a small data processing amount, and a computer-readable recording medium on which the posture estimation program is recorded.

Means for Solving the Problem

According to an aspect of the present invention, a posture estimation device includes: an acquisition part configured to acquire image data from an image sensor provided in a room; a storage configured to store information indicating a transition model of a human body posture and test information indicating a test area of the image data in each posture of the transition model; and an estimator configured to calculate a statistic in the test area of the image data by referring to the information indicating the transition model and the test information, and to estimate a current human body posture from the human body posture before one point of time based on the statistic.

Preferably, the estimator includes: a candidate specifying part configured to specify a candidate of a posture that can be changed from the human body posture before one point of time by referring to the information indicating the transition model; a test area specifying part configured to specify the test area of the image data by referring to the test information with respect to the specified candidate of the posture; a statistic calculator configured to calculate the statistic in the specified test area of the image data; and a determinator configured to determine whether the specified candidate of the posture is estimated as a current posture based on the calculated statistic.

Preferably, the statistic is a total value or an average value of pixel values in the test area.

Preferably, the determinator estimates the specified candidate of the posture as the current posture when the calculated statistic is greater than or equal to a reference value that is fixed according to the specified candidate of the posture.

Preferably, the image sensor is an infrared array sensor.

Preferably, a bed is disposed in the room, and the transition model of the posture includes the human body posture with respect to the bed.

Preferably, the acquisition part acquires first image data from a first image sensor provided in an upper portion of the room and second image data from a second image sensor provided in a side portion of the room, the storage stores test information indicating a test area of the first image data and a test area of the second image data in each posture of the transition model, and the estimator calculates statistics in the test area of the first image data and the test area of the second image data by referring to the information indicating the transition model and the test information, and estimates the current human body posture from the human body posture before one point of time using the calculated statistics.

Preferably, when the human body posture before one point of time is absence in the room in the transition model of the posture, a candidate of a posture that can be changed from the human body posture includes presence in the room.

Preferably, when the human body posture before one point of time is presence in the room in the transition model of the posture, a candidate of a posture that can be changed from the human body posture includes at least one of standing beside the bed, falling down, and absence in the room.

Preferably, when the human body posture before one point of time is standing beside the bed in the transition model of the posture, a candidate of a posture that can be changed from the human body posture includes at least one of lying on the bed, sitting on the bed, sitting on an edge of the bed, falling down, and presence in the room.

Preferably, when the human body posture before one point of time is lying on the bed in the transition model of the posture, a candidate of a posture that can be changed from the human body posture includes at least one of sitting on the bed, sitting on an edge of the bed, standing beside the bed, and falling from the bed.

Preferably, when the human body posture before one point of time is sitting on the bed in the transition model of the posture, a candidate of a posture that can be changed from the human body posture includes at least one of lying on the bed, sitting on an edge of the bed, standing beside the bed, and falling from the bed.

Preferably, when the human body posture before one point of time is sitting on an edge of the bed in the transition model of the posture, a candidate of a posture that can be changed from the human body posture includes at least one of lying on the bed, sitting on the bed, standing beside the bed, and falling from the bed.

Preferably, a posture identical to the human body posture before one point of time is included as the candidate of the posture that can be changed from the human body posture before one point of time in the transition model of the posture.

Preferably, when the candidate of the posture is absence in the room, the test area of the first image data is a whole area of the first image data, and the test area of the second image data is a whole area of the second image data.

Preferably, when the candidate of the posture is presence in the room, the test area of the first image data is a whole area of the first image data, and the test area of the second image data is a whole area of the second image data.

Preferably, when the candidate of the posture is standing beside the bed, the test area of the first image data is an area having a predetermined width from a position adjacent to a boundary in a longitudinal direction of an area corresponding to the bed, and a range in a vertical direction of the test area of the second image data is a whole range, and a range in a horizontal direction is a range having a predetermined width from a position adjacent to a range corresponding to the bed.

Preferably, when the candidate of the posture is falling down, the test area of the first image data is an area where an area corresponding to the bed is excluded from a whole area, and a range in a horizontal direction of the test area of the second image data is an area where a range corresponding to the bed is excluded from a whole range, and a range in a vertical direction is a range having a predetermined width upward from a lowest position.

Preferably, when the candidate of the posture is lying on the bed, the test area of the first image data is an area corresponding to the bed, and a range in a vertical direction of the test area of the second image data is a range having a predetermined first width from a position adjacent to a boundary above a range corresponding to the bed, and a range in a vertical direction is a range identical to a range corresponding to the bed.

Preferably, when the candidate of the posture is sitting on the bed, the test area of the first image data is an area corresponding to the bed, and a range in a vertical direction of the test area of the second image data is a range having a predetermined second width from a position adjacent to a boundary above a range corresponding to the bed, and a range in a vertical direction is a range identical to a range corresponding to the bed.

Preferably, when the candidate of the posture is sitting on an edge of the bed, the test area of the first image data is an area corresponding to the bed, and a range in a vertical direction of the test area of the second image data is a whole range, and a range in a horizontal direction is a range having a predetermined width from a position adjacent to a range corresponding to the bed.

Preferably, when the candidate of the posture is falling from the bed, the test area of the first image data is an area having a predetermined width from a position adjacent to a boundary in a longitudinal direction of an area corresponding to the bed, and a range in a horizontal direction of the test area of the second image data is a range where a range corresponding to the bed is excluded from a whole range, and a range in a vertical direction is a range having a predetermined width upward from a predetermined position.

According to another aspect of the present invention, a posture estimation system includes: an image sensor provided in a room; an acquisition part configured to acquire image data from the image sensor; a storage configured to store information indicating a transition model of a human body posture and test information indicating a test area of the image data in each posture of the transition model; and an estimator configured to calculate a statistic in the test area of the image data by referring to the information indicating the transition model and the test information, and to estimate a current human body posture from the human body posture before one point of time based on the statistic.

According to still another aspect of the present invention, a posture estimation method includes the steps of: generating image data by capturing an image of an inside of a room with an image sensor provided in the room; and calculating a statistic in a test area of the image data by referring to information indicating a transition model of a human body posture and test information indicating a test area of the image data in each posture of the transition model to estimate a current human body posture from the human body posture before one point of time based on the statistic.

According to still another aspect of the present invention, a posture estimation program causes a computer to function as: an acquisition part configured to acquire image data from an image sensor provided in a room; a storage configured to store information indicating a transition model of a human body posture and test information indicating a test area of the image data in each posture of the transition model; and an estimator configured to calculate a statistic in the test area of the image data by referring to the information indicating the transition model and the test information, and to estimate a current human body posture from the human body posture before one point of time based on the statistic.

According to still another aspect of the present invention, a computer-readable recording medium on which a posture estimation program is recorded, the posture estimation program causes a computer to function as: an acquisition part configured to acquire image data from an image sensor provided in a room; a storage configured to store information indicating a transition model of a human body posture and test information indicating a test area of the image data in each posture of the transition model; and an estimator configured to calculate a statistic in the test area of the image data by referring to the information indicating the transition model and the test information, and to estimate a current human body posture from the human body posture before one point of time based on the statistic.

Effect of the Invention

According to the present invention, a posture of a human body can be estimated with a small data processing amount.

BRIEF DESCRIPTION OF THE DRAWINGS

FIG. 7 is a view illustrating a transition model of a human body posture.

FIG. 8 is a view illustrating transition model information.

FIG. 9 is a view illustrating area information indicating the test area of the first image data and the test area of the second image data in each posture of the transition model, and reference value information indicating a reference value used to determine a transition to each posture.

FIG. 15 is a flowchart illustrating a procedure to determine a transition destination from a posture (F).

MODE FOR CARRYING OUT THE INVENTION

Hereinafter, an embodiment of the present invention will be described with reference to the drawings.

In the following description, a monitoring target person means a resident, such as an elderly person, who needs nursing care, and an inside of a room means a space in which the monitoring target person resides.

Figure 1:
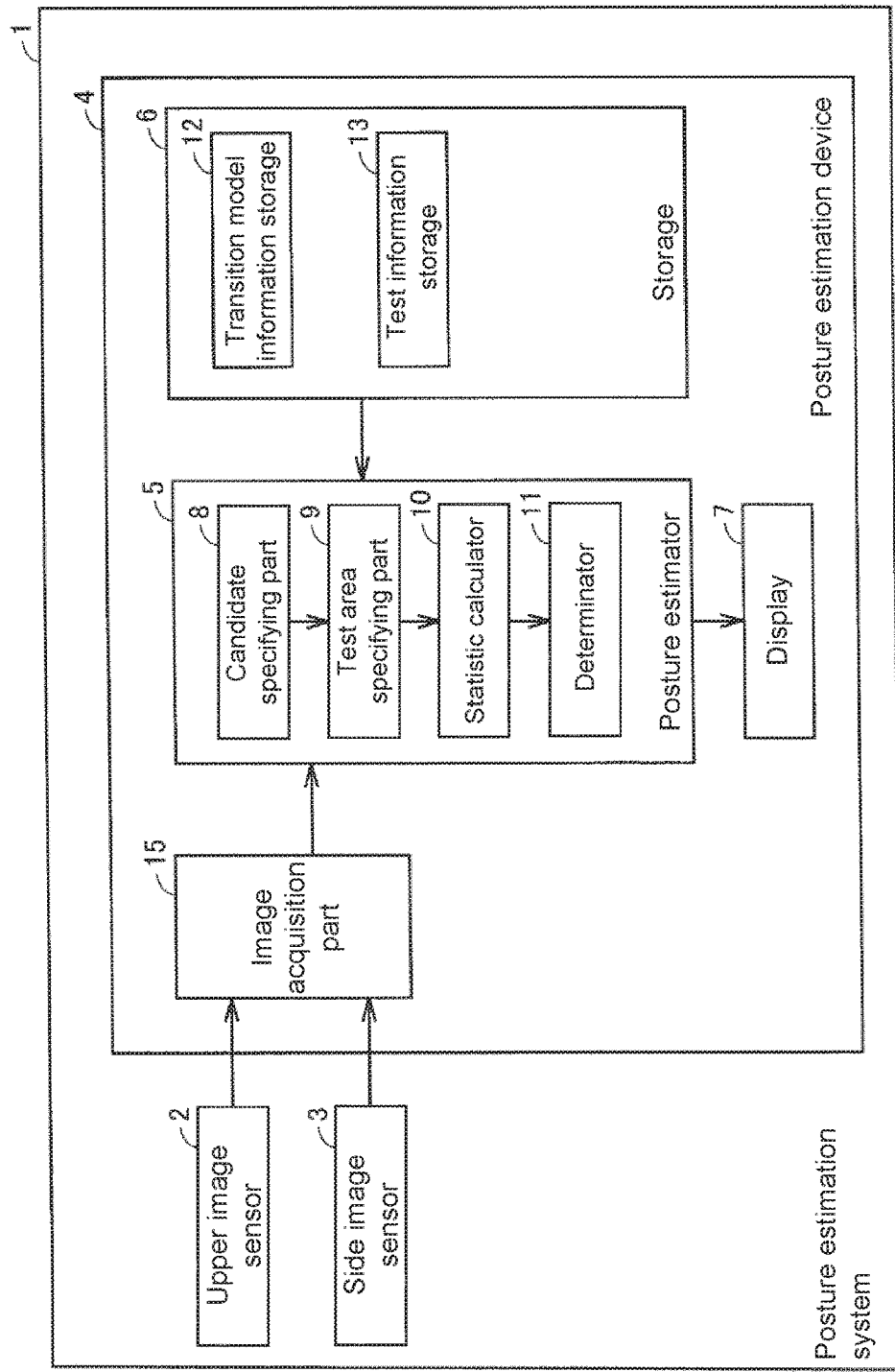
FIG. 1 is a view illustrating a configuration of a posture estimation system according to an embodiment of the present invention.

FIG. 1 is a view illustrating a configuration of a posture estimation system 1 according to an embodiment of the present invention.

As illustrated in FIG. 1, the posture estimation system 1 includes an upper image sensor 2, a side image sensor 3, and a posture estimation device 4.

The upper image sensor 2 is attached to an indoor ceiling to capture an indoor image from above. The side image sensor 3 is attached to an indoor side surface to capture an indoor image from the side. In the embodiment, the upper image sensor 2 and the side image sensor 3 are composed of an infrared array sensor. First image data output from the upper image sensor 2 is transmitted to the posture estimation device 4. Second image data output from the side image sensor 3 is transmitted to the posture estimation device 4.

In image data generated with the infrared array sensor, a temperature in an area where an image is captured increases with an increase of a pixel value, and the temperature decreases with a decrease of the pixel value. Because the temperature in an area where a human body is present is high, a pixel value in the area where the image of the human body is captured is high. Accordingly, the area where the human body is present can be specified by finding the area having the high pixel value from the image data.

The posture estimation device 4 includes an image acquisition part 15, a posture estimator 5, a storage 6, and a display 7. The posture estimator 5 includes a candidate specifying part 8, a test area specifying part 9, a statistic calculator 10, and a determinator 11. The storage 6 includes a transition model information storage 12 and a test information storage 13.

The image acquisition part 15 acquires the first image data from the upper image sensor 2 and the second image data from the side image sensor 3.

The transition model information storage 12 stores transition model information indicating the transition model of the human body posture. The test information storage 13 stores test information that includes area information and reference value information. The area information indicates the test area of the first image data and the test area of the second image data in each posture of the transition model. The reference value information indicates a reference value used to determine a transition to each posture. The transition model information and the test information are used to estimate a current human body posture. The transition model information and the test information will be described in detail later.

The candidate specifying part 8 refers to the transition model information to specify a candidate of a posture that can be changed from the human body posture before one point of time.

The test area specifying part 9 refers to the area information about the specified posture candidate to specify the test area of the first image data and the test area of the second image data.

The statistic calculator 10 calculates a statistic in the specified test area of the first image data and a statistic of the first image data.

The determinator 11 refers to the reference value information to determine whether the specified posture candidate is estimated as a current posture based on the calculated statistics.

A computer (not illustrated) executes a posture estimation program to implement the posture estimation device 4. In other words, the posture estimation program causes the computer to function as the image acquisition part 15, the posture estimator 5, the storage 6, and the display 7. The posture estimation program is recorded on the computer-readable recording medium such as a memory card, a CD-ROM, or a DVD, and is installed in the computer.

Figure 2:
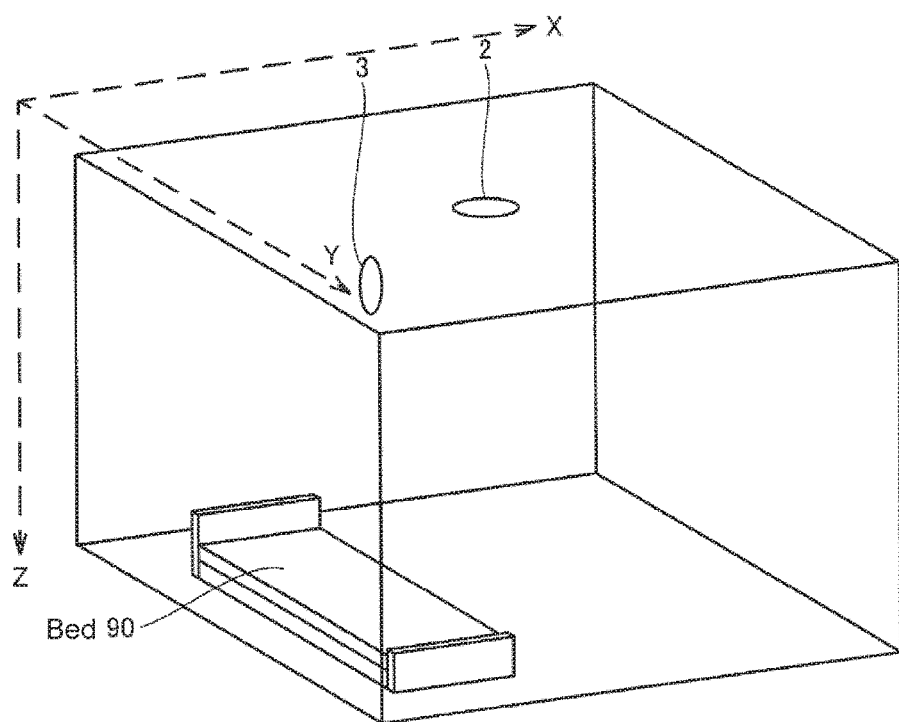
FIG. 2 is a cubic diagram illustrating an inside of a room.

FIG. 2 is a cubic diagram illustrating the inside of the room.

As illustrated in FIG. 2, the upper image sensor 2 is disposed in an upper portion of the inside of the room and the side image sensor 3 is disposed in a side portion of the inside of the room. A bed 90 is provided in the room. An indoor coordinate system X-Y-Z is illustrated in FIG. 2.

Figures 3, 4:
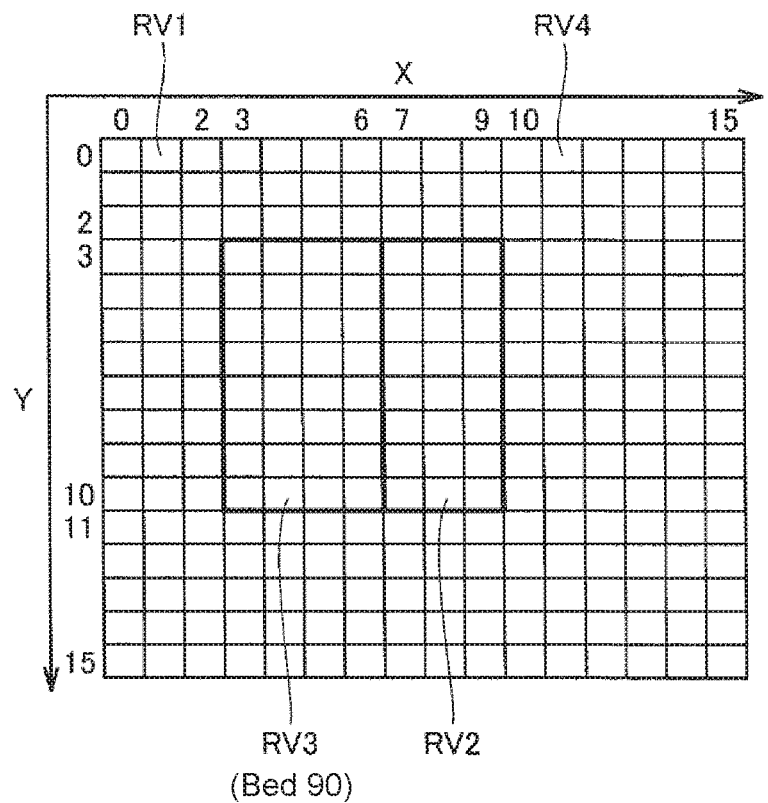
FIG. 3 is a view for describing first image data and a test area of the first image data.
FIG. 4 is a view for describing the first image data and the test area of the first image data.

FIGS. 3 and 4 are views for describing the first image data and the test area of the first image data. The first image data is made up of 16 pixels in an X-direction and 16 pixels in a Y-direction.

An area RV1 is a whole area of the first image data, namely, an area having a range of $0 \leq X \leq 15$ and $0 \leq Y \leq 15$.

An area RV2 is an area having a predetermined width (3 pixels) from a position adjacent to a boundary in a longitudinal direction of an area corresponding to the bed, namely, an area having a range of $7 \leq X \leq 9$ and $3 \leq Y \leq 10$.

An area RV3 is the area corresponding to the bed, namely, an area having a range of $3 \leq X \leq 6$ and $3 \leq Y \leq 10$.

An area RV4 is an area except for the area RV3, and is made up of four areas. A first area is an area having a range of $0 \leq X \leq 2$ and $0 \leq Y \leq 15$. A second area is an area having a range of $7 \leq X \leq 15$ and $0 \leq Y \leq 15$. A third area is an area having a range of $3 \leq X \leq 6$ and $0 \leq Y \leq 2$. A fourth area is an area having a range of $3 \leq X \leq 6$ and $11 \leq Y \leq 15$.

Figures 5, 6:
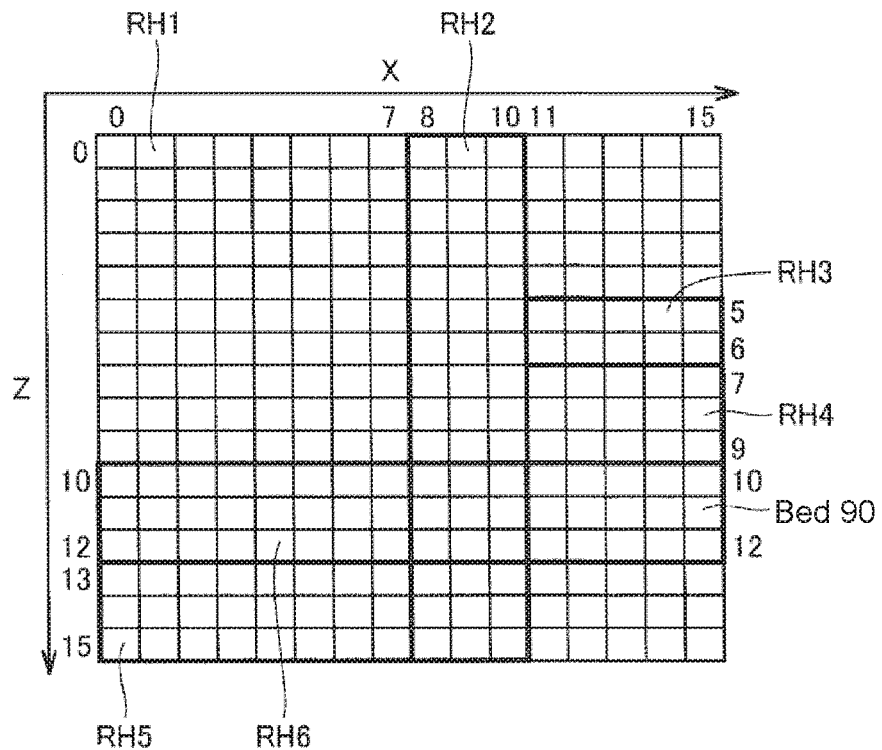
FIG. 5 is a view for describing second image data and the test area of the second image data.
FIG. 6 is a view for describing the second image data and the test area of the second image data.

FIGS. 5 and 6 are views for describing the second image data and the test area of the second image data. The second image data is made up of 16 pixels in the X-direction and 16 pixels in a Z-direction.

An area RH1 is a whole area of the second image data, namely, an area having a range of $0 \leq X \leq 15$ and $0 \leq Z \leq 15$.

A range in a vertical direction (Z-direction) of an area RH2 is a whole range. A range in a horizontal direction (X-direction) of the area RH2 is a range having a predetermined width (3 pixels) from a position adjacent to a range ($11 \leq X \leq 15$) corresponding to the bed. Accordingly, the area RH2 is an area having a range of $8 \leq X \leq 10$ and $0 \leq Z \leq 15$.

A range in the vertical direction (Z-direction) of an area RH3 is a range having a predetermined width (5 pixels) from a position adjacent to an upper boundary of the range corresponding to the bed. A range in the horizontal direction (X-direction) of the area RH3 is equal to the range corresponding to the bed. Accordingly, the area RH3 is an area having a range of $11 \leq X \leq 15$ and $5 \leq Z \leq 9$.

A range in the vertical direction (Z-direction) of an area RH4 is a range having a predetermined width (3 pixels) from the position adjacent to the upper boundary of the range corresponding to the bed. A range in the horizontal direction (X-direction) of the area RH4 is equal to the range corresponding to the bed. Accordingly, the area RH4 is an area having a range of $11 \leq X \leq 15$ and $7 \leq Z \leq 9$.

A range in the horizontal direction of an area RH5 is a range where the range corresponding to the bed is excluded from the whole range. A range in the vertical direction of the area RH5 is a range having a predetermined width (6 pixels) upward from the lowest position (Z=15). Accordingly, the area RH5 is an area having a range of $0 \leq X \leq 10$ and $10 \leq Z \leq 15$.

A range in the horizontal direction of an area RH6 is a range where the range corresponding to the bed is excluded from the whole range. A range in the vertical direction of the area RH6 is a range having a predetermined width (3 pixels) upward from a predetermined position (Z=12). Accordingly, the area RH6 is an area having a range of $0 \leq X \leq 10$ and $10 \leq Z \leq 12$.

FIG. 7 is a view illustrating the transition model of the human body posture. FIG. 8 is a view illustrating the transition model information.

A state in which the monitoring target person is absent in the room (A) is assumed as an initial state.

The next posture of the posture (A) is presence in the room (B) or the original posture (A).

The next posture of the posture (B) is standing beside the bed (C), falling down (X), absence in the room (A), or the original posture (B).

The next posture of the posture (C) is lying on the bed (D), sitting on the bed (E), sitting on an edge of the bed (F), falling down (X), presence in the room (B), or the original posture (C).

The next posture of the posture (D) is sitting on the bed (E), sitting on the edge of the bed (F), standing beside the bed (C), falling from the bed (first pattern) (Y1), or the original posture (D).

The next posture of the posture (E) is lying on the bed (D), sitting on the edge of the bed (F), standing beside the bed (C), falling from the bed (first pattern) (Y1), or the original posture (E).

The next posture of the posture (F) is lying on the bed (D), sitting on the bed (E), standing beside the bed (C), falling from the bed (second pattern) (Y2), or the original posture (F).

FIG. 9 is a view illustrating the area information indicating the test area of the first image data and the test area of the second image data in each posture of the transition model, and the reference value information indicating the reference value used to determine the transition to each posture.

The sum of the statistic in the area RV1 of the first image data and the statistic in the area RH1 of the second image data is calculated in order to determine the transition to the absence in the room (A). When the sum of the statistics is greater than or equal to a reference value THA, it is determined that the current posture is changed to the posture (A).

The sum of the statistic in the area RV1 of the first image data and the statistic in the area RH1 of the second image data is calculated in order to determine the transition to the presence in the room (B). When the sum of the statistics is greater than or equal to a reference value THB, it is determined that the current posture is changed to the posture (B).

The sum of the statistic in the area RV2 of the first image data and the statistic in the area RH2 of the second image data is calculated in order to determine the transition to the posture of standing beside the bed (C). When the sum of the statistics is greater than or equal to a reference value THC, it is determined that the current posture is changed to the posture (C).

The sum of the statistic in the area RV3 of the first image data and the statistic in the area RH4 of the second image data is calculated in order to determine the transition to the posture of lying on the bed (D). When the sum of the statistics is greater than or equal to a reference value THD, it is determined that the current posture is changed to the posture (D).

The sum of the statistic in the area RV3 of the first image data and the statistic in the area RH3 of the second image data is calculated in order to determine the transition to the posture of sitting on the bed (E). When the sum of the statistics is greater than or equal to a reference value THE, it is determined that the current posture is changed to the posture (E).

The sum of the statistic in the area RV3 of the first image data and the statistic in the area RH2 of the second image data is calculated in order to determine the transition to the posture of sitting on the edge of the bed (F). When the sum of the statistics is greater than or equal to a reference value THF, it is determined that the current posture is changed to the posture (F).

The sum of the statistic in the area RV4 of the first image data and the statistic in the area RH5 of the second image data is calculated in order to determine the transition to the posture of falling down (X). When the sum of the statistics is greater than or equal to a reference value THX, it is determined that the current posture is changed to the posture (X).

The sum of the statistic in the area RV2 of the first image data and the statistic in the area RH6 of the second image data is calculated in order to determine the transition to the posture of falling from the bed (first pattern) (Y1). When the sum of the statistics is greater than or equal to a reference value THY1, it is determined that the current posture is changed to the posture (Y1). The reason the area RH6 is used is that, because of a short distance between a place where the side image sensor 3 is disposed and a place where the monitoring target person falls from the bed, a portion where the image of the monitoring target person who falls from the bed is captured is positioned higher than the lowest line (Y=15) in the second image data.

The sum of the statistic in the area RV2 of the first image data and the statistic in the area RH6 of the second image data is calculated in order to determine the transition to the posture of falling from the bed (second pattern) (Y2). When the sum of the statistics is greater than or equal to a reference value THY2, it is determined that the current posture is changed to the posture (Y2). The reason the area RH6 is used is the same as the reason in the case for the posture of falling from the bed (first pattern).

(Transition from Posture A)

Figure 10:
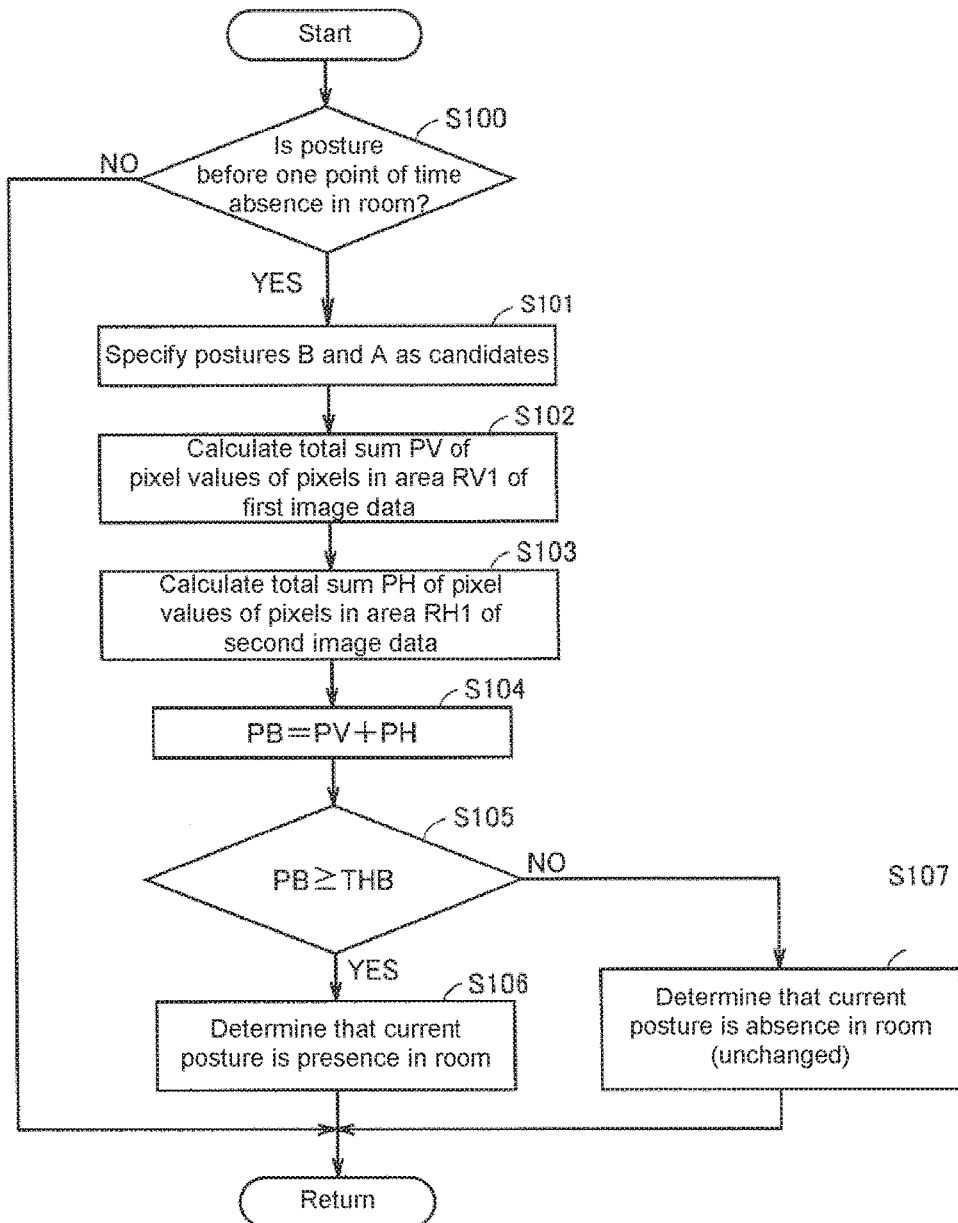
FIG. 10 is a flowchart illustrating a procedure to determine a transition destination from a posture (A).

FIG. 10 is a flowchart illustrating a procedure to determine a transition destination from the posture (A).

In step S100, the processing proceeds to step S101 when the posture before one point of time is the absence in the room (A).

In step S101, the candidate specifying part 8 refers to sequence information shown in FIG. 8 to specify the posture (B) and the posture (A) as candidates of the transition destination from the posture (A).

In step S102, the test area specifying part 9 refers to the test information shown in FIG. 9 to specify the area RV1 as the test area of the first image data for the posture (B). The statistic calculator 10 calculates a total sum PV of the pixel values of the pixels in the area RV1 of the first image data.

In step S103, the test area specifying part 9 refers to the test information shown in FIG. 9 to specify the area RH1 as the test area of the second image data for the posture (B). The statistic calculator 10 calculates a total sum PH of the pixel values of the pixels in the area RH1 of the second image data.

In step S104, the statistic calculator 10 calculates a sum PB of the total sum PV and the total sum PH.

In step S105, the determinator 11 compares the sum PB to the reference value THB. When the sum PB is greater than or equal to the reference value THB, the processing proceeds to step S106. When the sum PB is less than the reference value THB, the processing proceeds to step S107.

In step S106, the determinator 11 determines that the current posture is the presence in the room (B).

In step S107, the determinator 11 determines that the current posture is not the posture (B) but the posture before one point of time (A) that is a remaining candidate.

(Transition from Posture B)

Figure 11:
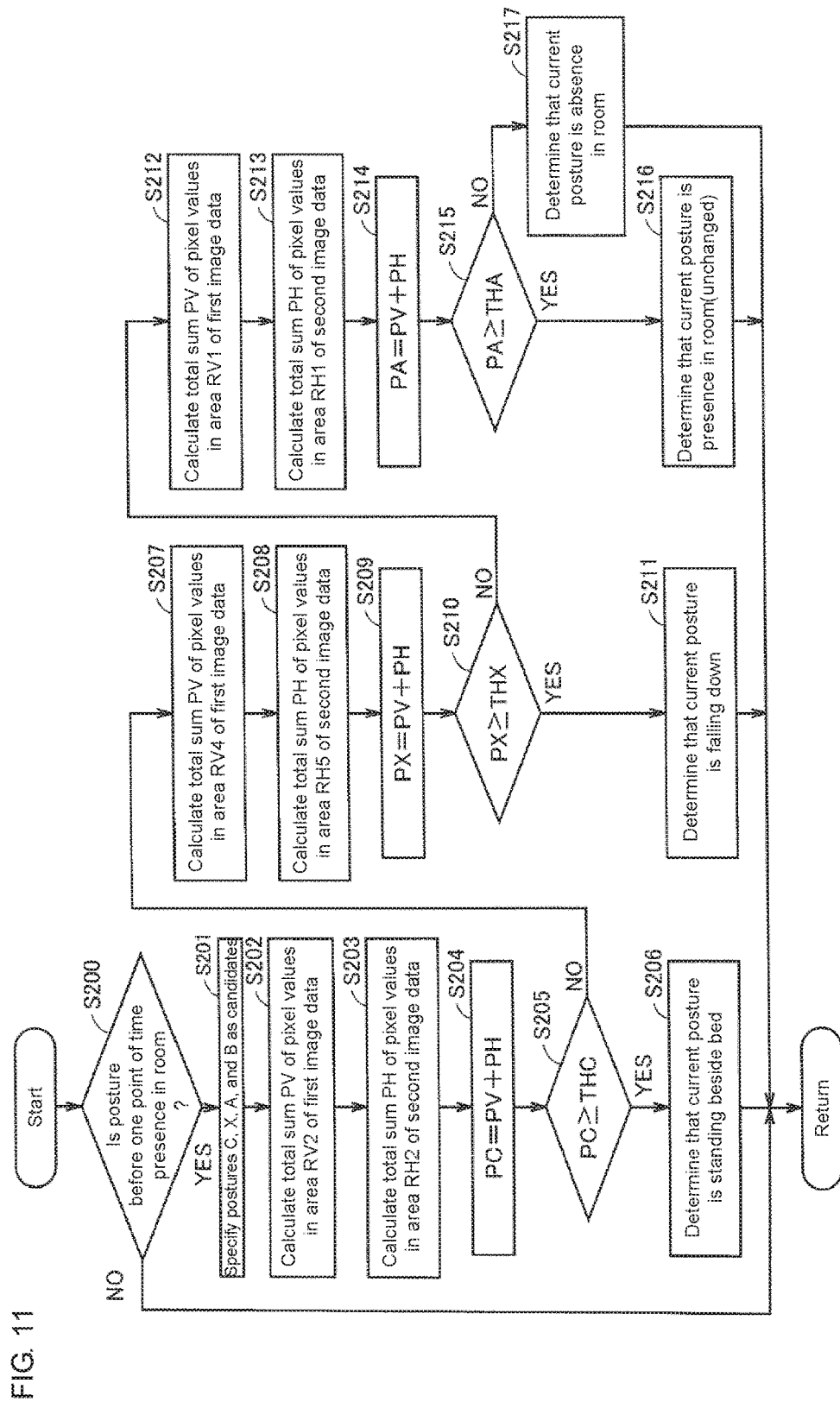
FIG. 11 is a flowchart illustrating a procedure to determine a transition destination from a posture (B).

FIG. 11 is a flowchart illustrating a procedure to determine the transition destination from the posture (B).

In step S200, the processing proceeds to step S201 when the posture before one point of time is the presence in the room (B).

In step S201, the candidate specifying part 8 refers to the sequence information shown in FIG. 8 to specify the posture (C), the posture (X), the posture (A), and the posture (B) as the candidates of the transition destination from the posture (B).

In step S202, the test area specifying part 9 refers to the test information shown in FIG. 9 to specify the area RV2 as the test area of the first image data for the posture (C). The statistic calculator 10 calculates the total sum PV of the pixel values of the pixels in the area RV2 of the first image data.

In step S203, the test area specifying part 9 refers to the test information shown in FIG. 9 to specify the area RH2 as the test area of the second image data for the posture (C). The statistic calculator 10 calculates the total sum PH of the pixel values of the pixels in the area RH2 of the second image data.

In step S204, the statistic calculator 10 calculates a sum PC of the total sum PV and the total sum PH.

In step S205, the determinator 11 compares the sum PC to the reference value THC. When the sum PC is greater than or equal to the reference value THC, the processing proceeds to step S206. When the sum PC is less than the reference value THC, the processing proceeds to step S207.

In step S206, the determinator 11 determines that the current posture is standing beside the bed (C).

In step S207, the test area specifying part 9 refers to the test information shown in FIG. 9 to specify the area RV4 as the test area of the first image data for the posture (X). The statistic calculator 10 calculates the total sum PV of the pixel values of the pixels in the area RV4 of the first image data.

In step S208, the test area specifying part 9 refers to the test information shown in FIG. 9 to specify the area RH5 as the test area of the second image data for the posture (X). The statistic calculator 10 calculates the total sum PH of the pixel values of the pixels in the area RH5 of the second image data.

In step S209, the statistic calculator 10 calculates a sum PX of the total sum PV and the total sum PH.

In step S210, the determinator 11 compares the sum PX to the reference value THX. When the sum PX is greater than or equal to the reference value THX, the processing proceeds to step S211. When the sum PX is less than the reference value THX, the processing proceeds to step S212.

In step S211, the determinator 11 determines that the current posture is falling down (X).

In step S212, the test area specifying part 9 refers to the test information in FIG. 9 to specify the area RV1 as the test area of the first image data for the posture (A). The statistic calculator 10 calculates a total sum PV of the pixel values of the pixels in the area RV1 of the first image data.

In step S213, the test area specifying part 9 refers to the test information shown in FIG. 9 to specify the area RH1 as the test area of the second image data for the posture (A). The statistic calculator 10 calculates a total sum PH of the pixel values of the pixels in the area RH1 of the second image data.

In step S214, the statistic calculator 10 calculates a sum PA of the total sum PV and the total sum PH.

In step S215, the determinator 11 compares the sum PA to the reference value THA. When the sum PA is greater than or equal to the reference value THA, the processing proceeds to step S216. When the sum PA is less than the reference value THA, the processing proceeds to step S217.

In step S216, the determinator 11 determines that the current posture is not the posture (C), the posture (X), or the posture (A), but the posture before one point of time (B) (presence in the room) that is the remaining candidate.

In step S217, the determinator 11 determines that the current posture is the absence in the room (A).

(Transition from Posture C)

Figure 12:
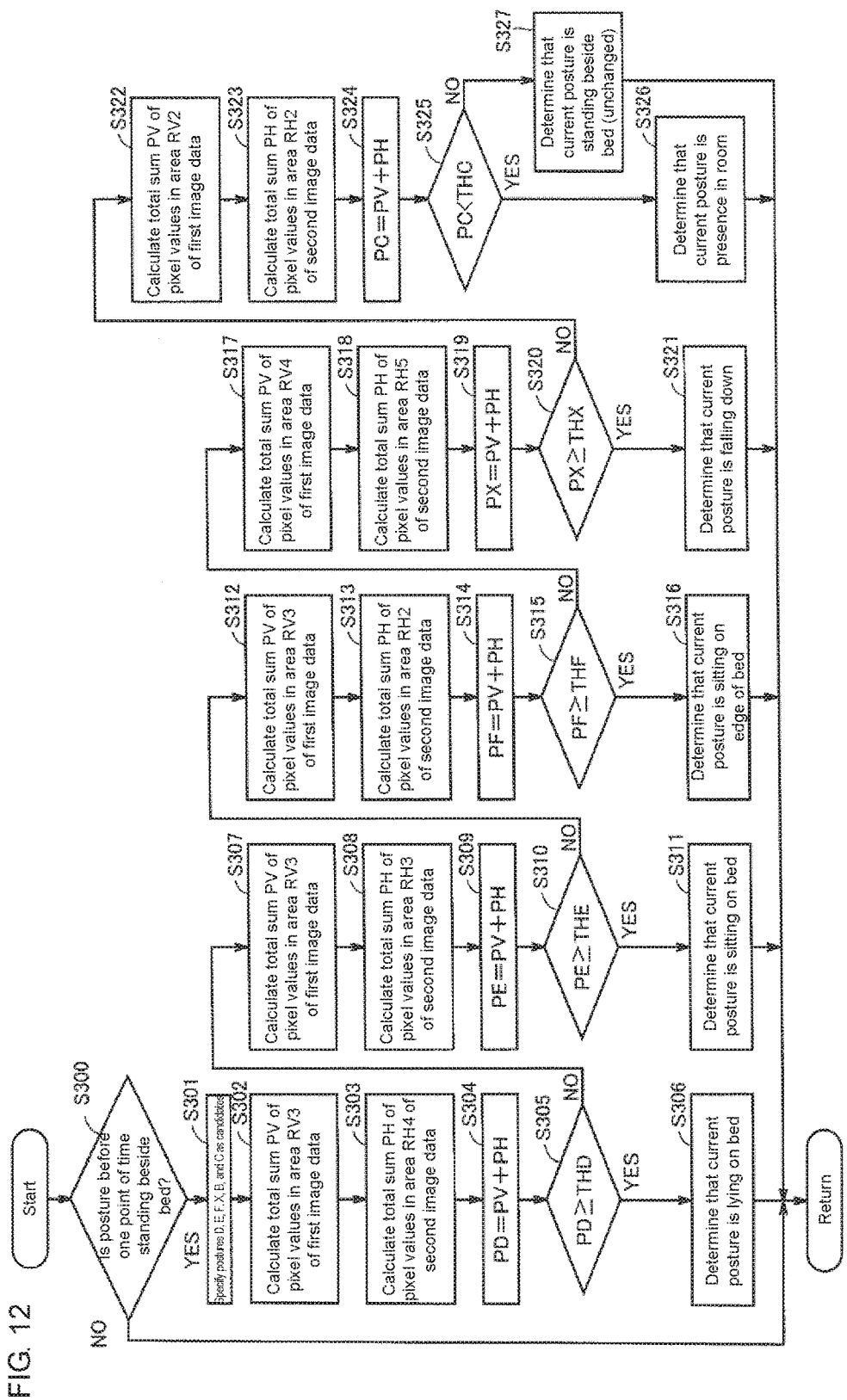
FIG. 12 is a flowchart illustrating a procedure to determine a transition destination from a posture (C).

FIG. 12 is a flowchart illustrating a procedure to determine the transition destination from the posture (C).

In step S300, the processing proceeds to step S301 when the posture before one point of time is standing beside the bed (C).

In step S301, the candidate specifying part 8 refers to the sequence information shown in FIG. 8 to specify the posture (D), the posture (E), the posture (F), the posture (X), the posture (B), and the posture (C) as the candidates of the transition destination from the posture (C).

In step S302, the test area specifying part 9 refers to the test information shown in FIG. 9 to specify the area RV3 as the test area of the first image data for the posture (D). The statistic calculator 10 calculates the total sum PV of the pixel values of the pixels in the area RV3 of the first image data.

In step S303, the test area specifying part 9 refers to the test information shown in FIG. 9 to specify the area RH4 as the test area of the second image data for the posture (D). The statistic calculator 10 calculates the total sum PH of the pixel values of the pixels in the area RH4 of the second image data.

In step S304, the statistic calculator 10 calculates a sum PD of the total sum PV and the total sum PH.

In step S305, the determinator 11 compares the sum PD to the reference value THD. When the sum PD is greater than or equal to the reference value THD, the processing proceeds to step S306. When the sum PD is less than the reference value THD, the processing proceeds to step S307.

In step S306, the determinator 11 determines that the current posture is lying on the bed (D).

In step S307, the test area specifying part 9 refers to the test information shown in FIG. 9 to specify the area RV3 as the test area of the first image data for the posture (E). The statistic calculator 10 calculates the total sum PV of the pixel values of the pixels in the area RV3 of the first image data.

In step S308, the test area specifying part 9 refers to the test information shown in FIG. 9 to specify the area RH3 as the test area of the second image data for the posture (E). The statistic calculator 10 calculates the total sum PH of the pixel values of the pixels in the area RH3 of the second image data.

In step S309, the statistic calculator 10 calculates a sum PE of the total sum PV and the total sum PH.

In step S310, the determinator 11 compares the sum PE to the reference value THE. When the sum PE is greater than or equal to the reference value THE, the processing proceeds to step S311. When the sum PE is less than the reference value THE, the processing proceeds to step S312.

In step S311, the determinator 11 determines that the current posture is sitting on the bed (E).

In step S312, the test area specifying part 9 refers to the test information shown in FIG. 9 to specify the area RV3 as the test area of the first image data for the posture (F). The statistic calculator 10 calculates the total sum PV of the pixel values of the pixels in the area RV3 of the first image data.

In step S313, the test area specifying part 9 refers to the test information shown in FIG. 9 to specify the area RH2 as the test area of the second image data for the posture (F). The statistic calculator 10 calculates the total sum PH of the pixel values of the pixels in the area RH2 of the second image data.

In step S314, the statistic calculator 10 calculates a sum PF of the total sum PV and the total sum PH.

In step S315, the determinator 11 compares the sum PF to the reference value THF. When the sum PF is greater than or equal to the reference value THF, the processing proceeds to step S316. When the sum PF is less than the reference value THF, the processing proceeds to step S317.

In step S316, the determinator 11 determines that the current posture is sitting on the edge of the bed (F).

In step S317, the test area specifying part 9 refers to the test information shown in FIG. 9 to specify the area RV4 as the test area of the first image data for the posture (X). The statistic calculator 10 calculates the total sum PV of the pixel values of the pixels in the area RV4 of the first image data.

In step S318, the test area specifying part 9 refers to the test information shown in FIG. 9 to specify the area RH5 as the test area of the second image data for the posture (X). The statistic calculator 10 calculates the total sum PH of the pixel values of the pixels in the area RH5 of the second image data.

In step S319, the statistic calculator 10 calculates the sum PX of the total sum PV and the total sum PH.

In step S320, the determinator 11 compares the sum PX to the reference value THX. When the sum PX is greater than or equal to the reference value THX, the processing proceeds to step S321. When the sum PX is less than the reference value THX, the processing proceeds to step S322.

In step S321, the determinator 11 determines that the current posture is falling down (X).

In step S322, the test area specifying part 9 refers to the test information shown in FIG. 9 to specify the area RV2 as the test area of the first image data for the posture (B). The statistic calculator 10 calculates the total sum PV of the pixel values of the pixels in the area RV2 of the first image data.

In step S323, the test area specifying part 9 refers to the test information shown in FIG. 9 to specify the area RH2 as the test area of the second image data for the posture (X). The statistic calculator 10 calculates the total sum PH of the pixel values of the pixels in the area RH2 of the second image data.

In step S324, the statistic calculator 10 calculates the sum PC of the total sum PV and the total sum PH.

In step S325, the determinator 11 compares the sum PC to the reference value THC. When the sum PC is less than the reference value THC, the processing proceeds to step S326. When the sum PC is greater than or equal to the reference value THC, the processing proceeds to step S327.

In step S326, the determinator 11 determines that the current posture is the presence in the room (B).

In step S327, the determinator 11 determines that the current posture is not the posture (D), the posture (E), the posture (F), the posture (X), or the posture (B), but the posture before one point of time (C) (standing beside the bed) that is the remaining candidate.

(Transition from Posture D)

Figure 13:
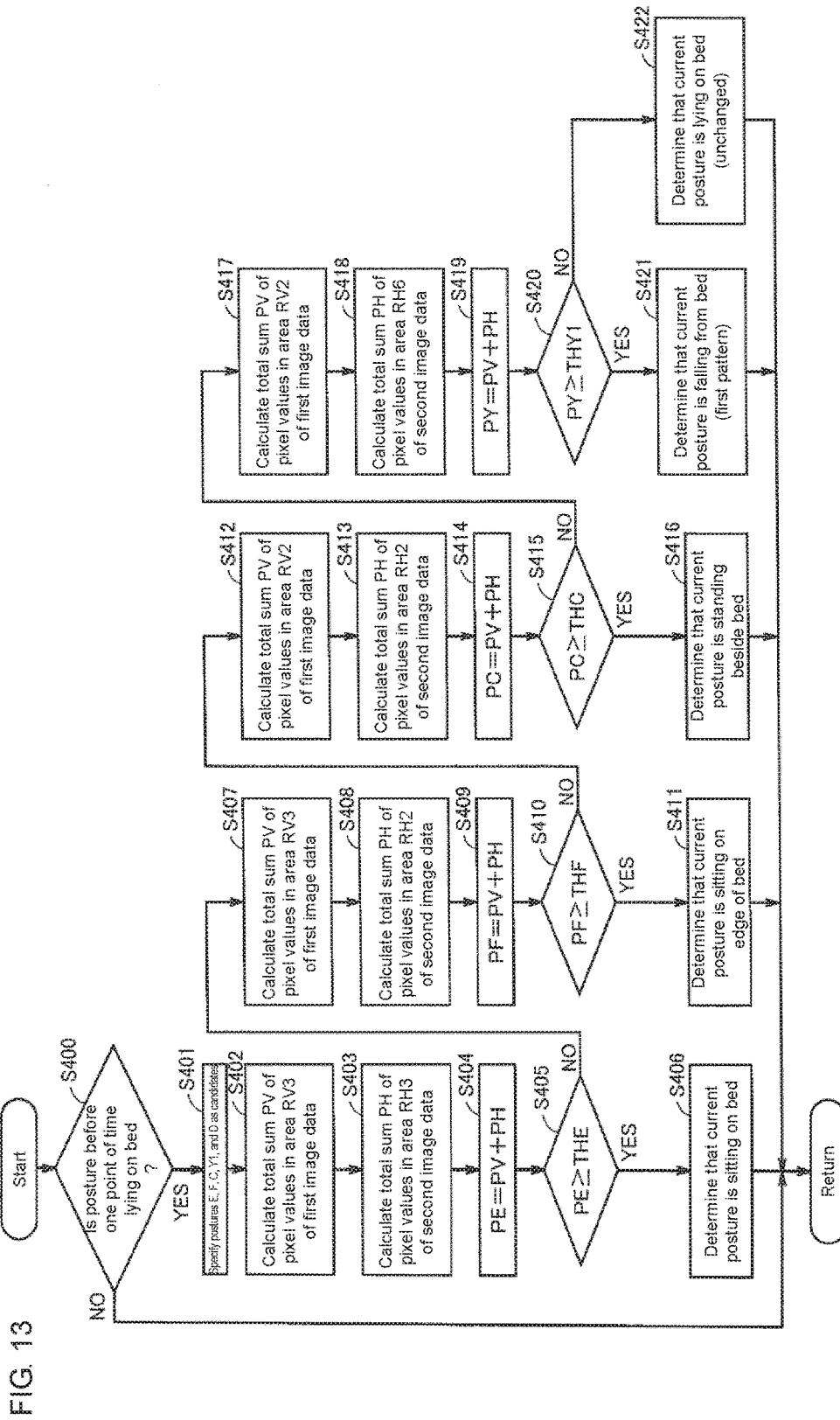
FIG. 13 is a flowchart illustrating a procedure to determine a transition destination from a posture (D).

FIG. 13 is a flowchart illustrating a procedure to determine the transition destination from the posture (D).

In step S400, the processing proceeds to step S401 when the posture before one point of time is lying on the bed (D).

In step S401, the candidate specifying part 8 refers to the sequence information shown in FIG. 8 to specify the posture (E), the posture (F), the posture (C), the posture (Y1), and the posture (D) as the candidates of the transition destination from the posture (D).

In step S402, the test area specifying part 9 refers to the test information shown in FIG. 9 to specify the area RV3 as the test area of the first image data for the posture (E). The statistic calculator 10 calculates the total sum PV of the pixel values of the pixels in the area RV3 of the first image data.

In step S403, the test area specifying part 9 refers to the test information shown in FIG. 9 to specify the area RH3 as the test area of the second image data for the posture (E). The statistic calculator 10 calculates the total sum PH of the pixel values of the pixels in the area RH3 of the second image data.

In step S404, the statistic calculator 10 calculates the sum PE of the total sum PV and the total sum PH.

In step S405, the determinator 11 compares the sum PE to the reference value THE. When the sum PE is greater than or equal to the reference value THE, the processing proceeds to step S406. When the sum PE is less than the reference value THE, the processing proceeds to step S407.

In step S406, the determinator 11 determines that the current posture is sitting on the bed (E).

In step S407, the test area specifying part 9 refers to the test information shown in FIG. 9 to specify the area RV3 as the test area of the first image data for the posture (F). The statistic calculator 10 calculates the total sum PV of the pixel values of the pixels in the area RV3 of the first image data.

In step S408, the test area specifying part 9 refers to the test information shown in FIG. 9 to specify the area RH2 as the test area of the second image data for the posture (F). The statistic calculator 10 calculates the total sum PH of the pixel values of the pixels in the area RH2 of the second image data.

In step S409, the statistic calculator 10 calculates the sum PF of the total sum PV and the total sum PH.

In step S410, the determinator 11 compares the sum PF to the reference value THF. When the sum PF is greater than or equal to the reference value THF, the processing proceeds to step S411. When the sum PF is less than the reference value THF, the processing proceeds to step S412.

In step S411, the determinator 11 determines that the current posture is sitting on the edge of the bed (F).

In step S412, the test area specifying part 9 refers to the test information shown in FIG. 9 to specify the area RV2 as the test area of the first image data for the posture (C). The statistic calculator 10 calculates the total sum PV of the pixel values of the pixels in the area RV2 of the first image data.

In step S413, the test area specifying part 9 refers to the test information shown in FIG. 9 to specify the area RH2 as the test area of the second image data for the posture (C). The statistic calculator 10 calculates the total sum PH of the pixel values of the pixels in the area RH2 of the second image data.

In step S414, the statistic calculator 10 calculates the sum PC of the total sum PV and the total sum PH.

In step S415, the determinator 11 compares the sum PC to the reference value THC. When the sum PC is greater than or equal to the reference value THC, the processing proceeds to step S416. When the sum PC is less than the reference value THC, the processing proceeds to step S417.

In step S416, the determinator 11 determines that the current posture is standing beside the bed (C).

In step S417, the test area specifying part 9 refers to the test information shown in FIG. 9 to specify the area RV2 as the test area of the first image data for the posture (Y1). The statistic calculator 10 calculates the total sum PV of the pixel values of the pixels in the area RV2 of the first image data.

In step S418, the test area specifying part 9 refers to the test information shown in FIG. 9 to specify the area RH6 as the test area of the second image data for the posture (Y1). The statistic calculator 10 calculates the total sum PH of the pixel values of the pixels in the area RH6 of the second image data.

In step S419, the statistic calculator 10 calculates a sum PY1 of the total sum PV and the total sum PH.

In step S420, the determinator 11 compares the sum PY1 to the reference value THY1. When the sum PY1 is greater than or equal to the reference value THY1, the processing proceeds to step S421. When the sum PY1 is less than the reference value THY1, the processing proceeds to step S422.

In step S421, the determinator 11 determines that the current posture is falling from the bed (first pattern) (Y1).

In step S422, the determinator 11 determines that the current posture is not the posture (E), the posture (F), the posture (C), or the posture (Y1), but the posture before one point of time (D) that is the remaining candidate.

(Transition from Posture E)

Figure 14:
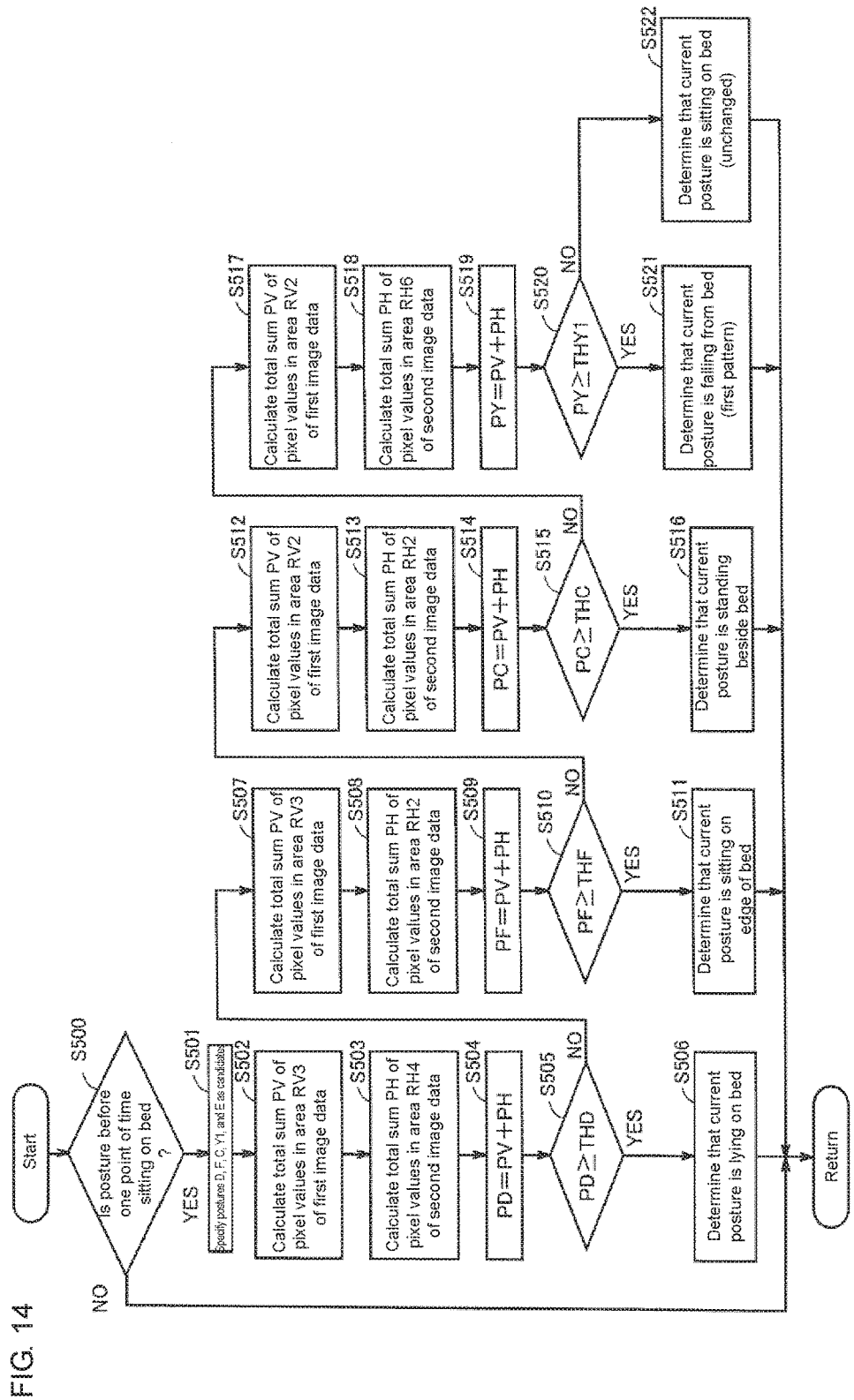
FIG. 14 is a flowchart illustrating a procedure to determine a transition destination from a posture (E).

FIG. 14 is a flowchart illustrating a procedure to determine the transition destination from the posture (E).

In step S500, the processing proceeds to step S501 when the posture before one point of time is sitting on the bed (E).

In step S501, the candidate specifying part 8 refers to the sequence information shown in FIG. 8 to specify the posture (D), the posture (F), the posture (C), the posture (Y1), and the posture (E) as the candidates of the transition destination from the posture (E).

In step S502, the test area specifying part 9 refers to the test information shown in FIG. 9 to specify the area RV3 as the test area of the first image data for the posture (D). The statistic calculator 10 calculates the total sum PV of the pixel values of the pixels in the area RV3 of the first image data.

In step S503, the test area specifying part 9 refers to the test information shown in FIG. 9 to specify the area RH4 as the test area of the second image data for the posture (D). The statistic calculator 10 calculates the total sum PH of the pixel values of the pixels in the area RH4 of the second image data.

In step S504, the statistic calculator 10 calculates the sum PD of the total sum PV and the total sum PH.

In step S505, the determinator 11 compares the sum PD to the reference value THD. When the sum PD is greater than or equal to the reference value THD, the processing proceeds to step S506. When the sum PD is less than the reference value THD, the processing proceeds to step S507.

In step S506, the determinator 11 determines that the current posture is lying on the bed (D).

In step S507, the test area specifying part 9 refers to the test information shown in FIG. 9 to specify the area RV3 as the test area of the first image data for the posture (F). The statistic calculator 10 calculates the total sum PV of the pixel values of the pixels in the area RV3 of the first image data.

In step S508, the test area specifying part 9 refers to the test information shown in FIG. 9 to specify the area RH2 as the test area of the second image data for the posture (F). The statistic calculator 10 calculates the total sum PH of the pixel values of the pixels in the area RH2 of the second image data.

In step S509, the statistic calculator 10 calculates the sum PF of the total sum PV and the total sum PH.

In step S510, the determinator 11 compares the sum PF to the reference value THF. When the sum PF is greater than or equal to the reference value THF, the processing proceeds to step S511. When the sum PF is less than the reference value THF, the processing proceeds to step S512.

In step S511, the determinator 11 determines that the current posture is sitting on the edge of the bed (F).

In step S512, the test area specifying part 9 refers to the test information shown in FIG. 9 to specify the area RV2 as the test area of the first image data for the posture (C). The statistic calculator 10 calculates the total sum PV of the pixel values of the pixels in the area RV2 of the first image data.

In step S513, the test area specifying part 9 refers to the test information shown in FIG. 9 to specify the area RH2 as the test area of the second image data for the posture (C). The statistic calculator 10 calculates the total sum PH of the pixel values of the pixels in the area RH2 of the second image data.

In step S514, the statistic calculator 10 calculates the sum PC of the total sum PV and the total sum PH.

In step S515, the determinator 11 compares the sum PC to the reference value THC. When the sum PC is greater than or equal to the reference value THC, the processing proceeds to step S516. When the sum PC is less than the reference value THC, the processing proceeds to step S517.

In step S516, the determinator 11 determines that the current posture is standing beside the bed (C).

In step S517, the test area specifying part 9 refers to the test information shown in FIG. 9 to specify the area RV2 as the test area of the first image data for the posture (Y1). The statistic calculator 10 calculates the total sum PV of the pixel values of the pixels in the area RV2 of the first image data.

In step S518, the test area specifying part 9 refers to the test information shown in FIG. 9 to specify the area RH6 as the test area of the second image data for the posture (Y1). The statistic calculator 10 calculates the total sum PH of the pixel values of the pixels in the area RH6 of the second image data.

In step S519, the statistic calculator 10 calculates the sum PY1 of the total sum PV and the total sum PH.

In step S520, the determinator 11 compares the sum PY1 to the reference value THY1. When the sum PY1 is greater than or equal to the reference value THY1, the processing proceeds to step S521. When the sum PY1 is less than the reference value THY1, the processing proceeds to step S522.

In step S521, the determinator 11 determines that the current posture is falling from the bed (first pattern) (Y1).

In step S522, the determinator 11 determines that the current posture is not the posture (D), the posture (F), the posture (C), or the posture (Y1), but the posture before one point of time (E) that is the remaining candidate.

(Transition from Posture F)

FIG. 15 is a flowchart illustrating a procedure to determine the transition destination from the posture (F).

In step S600, the processing proceeds to step S601 when the posture before one point of time is sitting on the edge of the bed (F).

In step S601, the candidate specifying part 8 refers to the sequence information shown in FIG. 8 to specify the posture (D), the posture (E), the posture (C), the posture (Y2), and the posture (F) as the candidates of the transition destination from the posture (F).

In step S602, the test area specifying part 9 refers to the test information shown in FIG. 9 to specify the area RV3 as the test area of the first image data for the posture (D). The statistic calculator 10 calculates the total sum PV of the pixel values of the pixels in the area RV3 of the first image data.

In step S603, the test area specifying part 9 refers to the test information shown in FIG. 9 to specify the area RH4 as the test area of the second image data for the posture (D). The statistic calculator 10 calculates the total sum PH of the pixel values of the pixels in the area RH4 of the second image data.

In step S604, the statistic calculator 10 calculates the sum PD of the total sum PV and the total sum PH.

In step S605, the determinator 11 compares the sum PD to the reference value THD. When the sum PD is greater than or equal to the reference value THD, the processing proceeds to step S606. When the sum PD is less than the reference value THD, the processing proceeds to step S607.

In step S606, the determinator 11 determines that the current posture is lying on the bed (D).

In step S607, the test area specifying part 9 refers to the test information shown in FIG. 9 to specify the area RV3 as the test area of the first image data for the posture (E). The statistic calculator 10 calculates the total sum PV of the pixel values of the pixels in the area RV3 of the first image data.

In step S608, the test area specifying part 9 refers to the test information shown in FIG. 9 to specify the area RH3 as the test area of the second image data for the posture (E). The statistic calculator 10 calculates the total sum PH of the pixel values of the pixels in the area RH2 of the second image data.

In step S609, the statistic calculator 10 calculates the sum PE of the total sum PV and the total sum PH.

In step S610, the determinator 11 compares the sum PE to the reference value THE. When the sum PE is greater than or equal to the reference value THE, the processing proceeds to step S611. When the sum PE is less than the reference value THE, the processing proceeds to step S612.

In step S611, the determinator 11 determines that the current posture is sitting on the bed (E).

In step S612, the test area specifying part 9 refers to the test information shown in FIG. 9 to specify the area RV2 as the test area of the first image data for the posture (C). The statistic calculator 10 calculates the total sum PV of the pixel values of the pixels in the area RV2 of the first image data.

In step S613, the test area specifying part 9 refers to the test information shown in FIG. 9 to specify the area RH2 as the test area of the second image data for the posture (C). The statistic calculator 10 calculates the total sum PH of the pixel values of the pixels in the area RH2 of the second image data.

In step S614, the statistic calculator 10 calculates the sum PC of the total sum PV and the total sum PH.

In step S615, the determinator 11 compares the sum PC to the reference value THC. When the sum PC is greater than or equal to the reference value THC, the processing proceeds to step S616. When the sum PC is less than the reference value THC, the processing proceeds to step S617.

In step S616, the determinator 11 determines that the current posture is standing beside the bed (C).

In step S617, the test area specifying part 9 refers to the test information shown in FIG. 9 to specify the area RV2 as the test area of the first image data for the posture (Y2). The statistic calculator 10 calculates the total sum PV of the pixel values of the pixels in the area RV2 of the first image data.

In step S618, the test area specifying part 9 refers to the test information shown in FIG. 9 to specify the area RH6 as the test area of the second image data for the posture (Y2). The statistic calculator 10 calculates the total sum PH of the pixel values of the pixels in the area RH6 of the second image data.

In step S619, the statistic calculator 10 calculates a sum PY2 of the total sum PV and the total sum PH.

In step S620, the determinator 11 compares the sum PY2 to the reference value THY2. When the sum PY2 is greater than or equal to the reference value THY2, the processing proceeds to step S621. When the sum PY2 is less than the reference value THY2, the processing proceeds to step S622.

In step S621, the determinator 11 determines that the current posture is falling from the bed (second pattern) (Y2).

In step S622, the determinator 11 determines that the current posture is not the posture (D), the posture (E), the posture (C), or the posture (Y2), but the posture before one point of time (F) that is the remaining candidate.

According to the embodiment, because the presence of the human body is detected only by obtaining the sum of the pixel values in the test area, it is not necessary to perform the image processing of specifying the area of the human body, unlike Patent Document 1. Resultantly, in the embodiment, the human body posture can be estimated in real time with a small calculation processing amount. According to the embodiment, by the use of the posture transition model, it is possible to estimate not only the behavior of rising from the bed as disclosed in Patent Document 1, but also more postures.

(Modifications)

The present invention is not limited to the above embodiment, but the following modifications can be made.

(1) Statistic

In the embodiment of the present invention, the total sum of the pixel values in the test area is used as the statistic, but the present invention is not limited thereto. For example, a mean or a variance of the pixel values in the test area may be used as the statistic.

Alternatively, the pixel value of standard image data or the pixel value of the image data in a preceding frame and the pixel value of current image data are subtracted, and the total sum, the average value, or the variance of the subtracted value may be used as the statistic. Therefore, the statistic increases immediately after the posture changes, timing immediately after the posture changes can be detected.

Alternatively, the total sum of the pixels having a predetermined pixel value or more (that is, the imaging target has a predetermined temperature or more) may be used as the statistic. In this case, the pixel values having predetermined bits or more are added, so that a calculation amount can further be reduced.

Further, the calculation amount may be reduced not by calculating the statistic from all the pixel values in the test area, but by calculating the statistic from the pixel values randomly sampled from the test area.

(2) Determinator

In the embodiment of the present invention, the sum of the statistic in the test area of the first image data and the statistic in the test area of the second image data is calculated, and the candidate is estimated as the current posture when the sum is greater than or equal to the reference value.

For example, when the statistic in the test area of the first image data is greater than or equal to a first reference value, and when the statistic in the test area of the second image data is greater than or equal to a second reference value, the candidate may be estimated as the current posture.

(3) The Number of Image Sensors

In the embodiment of the present invention, the human body posture is estimated with two image sensors. Alternatively, the human body posture can be estimated with one image sensor.

For example, the posture of falling from the bed may be estimated using only the image data obtained from the upper image sensor. Alternatively, the change in posture on the bed may be estimated using only the image data obtained from the side image sensor.

(4) Image Sensor

In the embodiment of the present invention, the upper image sensor and the side image sensor are composed of the infrared array sensor. However, the upper image sensor and the side image sensor may be composed of another sensor such as a visible-light camera.

(5) Posture

In the embodiment of the present invention, the human body posture relative to the bed is estimated, but the present invention is not limited thereto. For example, the human body posture relative to a chair or a wheel chair may be estimated.

(6) Determination Method

In the embodiment of the present invention, the plural candidates at the current time are sequentially selected one by one, and the selected candidate is estimated as the current posture when the statistic is greater than or equal to the reference value. However, the present invention is not limited thereto.

Alternatively, for example, the statistic is calculated for all the plural candidates at the current time, an optimum statistic is determined from the calculated plural statistics according to a predetermined criterion, and the candidate having the optimum statistic may be estimated as the current posture.

It is noted that the disclosed embodiment is not restrictive but illustrative in every respect. The scope of the present invention is indicated not by the above description but by the claims, and is intended to include all meanings equivalent to the claims and all modifications within the scope of the claims.

DESCRIPTION OF SYMBOLS 1 posture estimation system
2 upper image sensor
3 side image sensor
4 posture estimation device
5 posture estimator
6 storage
7 display
8 candidate specifying part
9 test area specifying part
10 statistic calculator
11 determinator
12 transition model information storage
13 test information storage

The invention claimed is:

1. A posture estimation device comprising:
an acquisition part configured to acquire image data from an image sensor provided in a room;
a storage configured to store information indicating a transition model of a human body posture and test information indicating a test area of the image data in each posture of the transition model; and
an estimator configured to calculate a statistic in the test area of the image data by referring to the information indicating the transition model and the test information, and to estimate a current human body posture from the human body posture before one point of time based on the statistic;
wherein the estimator comprises:
a candidate specifying part configured to specify a candidate of a posture that can be changed from the human body posture before one point of time by referring to the information indicating the transition model;
a test area specifying part configured to specify the test area of the image data by referring to the test information with respect to the specified candidate of the posture;
a statistic calculator configured to calculate the statistic in the specified test area of the image data; and
a determinator configured to determine whether the specified candidate of the posture is estimated as a current posture based on the calculated statistic.

2. The posture estimation device according to claim 1, wherein the statistic is a total value or an average value of pixel values in the test area.

3. The posture estimation device according to claim 1, wherein the determinator estimates the specified candidate of the posture as the current posture when the calculated statistic is greater than or equal to a reference value that is fixed according to the specified candidate of the posture.

4. The posture estimation device according to claim 1, wherein the image sensor is an infrared array sensor.

5. The posture estimation device according to claim 1, wherein
a bed is disposed in the room, and
the transition model of the posture includes the human body posture with respect to the bed.

6. A posture estimation device comprising:
an acquisition part configured to acquire image data from an image sensor provided in a room;
a storage configured to store information indicating a transition model of a human body posture and test information indicating a test area of the image data in each posture of the transition model; and
an estimator configured to calculate a statistic in the test area of the image data by referring to the information indicating the transition model and the test information, and to estimate a current human body posture from the human body posture before one point of time based on the statistic;
wherein
the acquisition part acquires first image data from a first image sensor provided in an upper portion of the room and second image data from a second image sensor provided in a side portion of the room,
the storage stores test information indicating a test area of the first image data and a test area of the second image data in each posture of the transition model, and
the estimator calculates statistics in the test area of the first image data and the test area of the second image data by referring to the information indicating the transition model and the test information, and estimates the current human body posture from the human body posture before one point of time using the calculated statistics.

7. The posture estimation device according to claim 6, wherein when the human body posture before one point of time is absence in the room in the transition model of the posture, a candidate of a posture that can be changed from the human body posture includes presence in the room.

8. The posture estimation device according to claim 6, wherein when the human body posture before one point of time is presence in the room in the transition model of the posture, a candidate of a posture that can be changed from the human body posture includes at least one of standing beside a bed, falling down, and absence in the room.

9. The posture estimation device according to claim 6, wherein when the human body posture before one point of time is standing beside a bed in the transition model of the posture, a candidate of a posture that can be changed from the human body posture includes at least one of lying on the bed, sitting on the bed, sitting on an edge of the bed, falling down, and presence in the room.

10. The posture estimation device according to claim 6, wherein when the human body posture before one point of time is lying on a bed in the transition model of the posture, a candidate of a posture that can be changed from the human body posture includes at least one of sitting on the bed, sitting on an edge of the bed, standing beside the bed, and falling from the bed.

11. The posture estimation device according to claim 6, wherein when the human body posture before one point of time is sitting on a bed in the transition model of the posture, a candidate of a posture that can be changed from the human body posture includes at least one of lying on the bed, sitting on an edge of the bed, standing beside the bed, and falling from the bed.

12. The posture estimation device according to claim 6, wherein when the human body posture before one point of time is sitting on an edge of a bed in the transition model of the posture, a candidate of a posture that can be changed from the human body posture includes at least one of lying on the bed, sitting on the bed, standing beside the bed, and falling from the bed.

13. The posture estimation device according to claim 6, wherein a posture identical to the human body posture before one point of time is comprised as the candidate of the posture that can be changed from the human body posture before one point of time in the transition model of the posture.

14. A posture estimation system comprising:
an image sensor provided in a room;
an acquisition part configured to acquire image data from the image sensor;
a storage configured to store information indicating a transition model of a human body posture and test information indicating a test area of the image data in each posture of the transition model; and
an estimator configured to calculate a statistic in the test area of the image data by referring to the information indicating the transition model and the test information, and to estimate a current human body posture from the human body posture before one point of time based on the statistic;
wherein the estimator comprises:
a candidate specifying part configured to specify a candidate of a posture that can be changed from the human body posture before one point of time by referring to the information indicating the transition model;
a test area specifying part configured to specify the test area of the image data by referring to the test information with respect to the specified candidate of the posture;
a statistic calculator configured to calculate the statistic in the specified test area of the image data; and
a determinator configured to determine whether the specified candidate of the posture is estimated as a current posture based on the calculated statistic.

15. A posture estimation method comprising the steps of:
generating image data by capturing an image of an inside of a room with an image sensor provided in the room; and
calculating a statistic in a test area of the image data by referring to information indicating a transition model of a human body posture and test information indicating a test area of the image data in each posture of the transition model to estimate a current human body posture from the human body posture before one point of time based on the statistic;
wherein the step of calculating comprises:
specifying a candidate of a posture that can be changed from the human body posture before one point of time by referring to the information indicating the transition model;
specifying the test area of the image data by referring to the test information with respect to the specified candidate of the posture;
calculating the statistic in the specified test area of the image data; and
determining whether the specified candidate of the posture is estimated as a current posture based on the calculated statistic.

16. A non-transitory computer-readable medium on which a posture estimation program is recorded, the posture estimation program causing a computer to function as:

an acquisition part configured to acquire image data from an image sensor provided in a room;

a storage configured to store information indicating a transition model of a human body posture and test information indicating a test area of the image data in each posture of the transition model; and an estimator configured to calculate a statistic in the test area of the image data by referring to the information indicating the transition model and the test information, and to estimate a current human body posture from the human body posture before one point of time based on the statistic;

wherein the estimator comprises:

a candidate specifying part configured to specify a candidate of a posture that can be changed from the human body posture before one point of time by referring to the information indicating the transition model;

a test area specifying part configured to specify the test area of the image data by referring to the test information with respect to the specified candidate of the posture;

a statistic calculator configured to calculate the statistic in the specified test area of the image data; and a determinator configured to determine whether the specified candidate of the posture is estimated as a current posture based on the calculated statistic.

* * * * *